United States Patent [19]
Hendler

[11] Patent Number: 5,981,603
[45] Date of Patent: Nov. 9, 1999

[54] ANTIVIRAL AGENTS

[75] Inventor: Sheldon S. Hendler, La Jolla, Calif.

[73] Assignee: Vyrex Corporation, LaJolla, Calif.

[21] Appl. No.: 08/808,554

[22] Filed: Feb. 28, 1997

Related U.S. Application Data

[63] Continuation of application No. 08/130,168, Sep. 30, 1993, which is a continuation of application No. 07/550,528, Jul. 10, 1990, abandoned, which is a continuation-in-part of application No. 07/452,737, Dec. 19, 1989, abandoned, which is a continuation-in-part of application No. 07/381,132, Jul. 14, 1989, Pat. No. 4,985,465.

[51] Int. Cl.$^6$ .................................................. A61K 31/10
[52] U.S. Cl. .......................................... 514/712; 514/713
[58] Field of Search ..................................... 514/712, 713

[56] References Cited

U.S. PATENT DOCUMENTS

| | | | |
|---|---|---|---|
| 3,129,262 | 4/1964 | Laufer et al. | 260/578 |
| 3,574,853 | 4/1971 | Barnhart | 260/609 |
| 3,576,883 | 4/1971 | Neuworth | 260/609 |
| 3,692,907 | 9/1972 | Fleming et al. | 424/248 |
| 3,862,332 | 12/1975 | Barnhart et al. | 424/337 |
| 3,956,359 | 5/1976 | Neuworth | 260/470 |
| 4,086,006 | 4/1978 | Leach | 514/712 |
| 4,115,590 | 9/1978 | Lerner | 424/337 |
| 4,192,896 | 3/1980 | Leach et al. | 514/712 |
| 4,350,707 | 9/1982 | Keith et al. | 424/346 |
| 4,560,799 | 12/1985 | Spivack et al. | 568/47 |
| 4,719,237 | 1/1988 | McCaughan | 514/712 |
| 4,835,190 | 5/1989 | Mueller et al. | 514/712 |
| 4,847,305 | 7/1989 | Mueller et al. | 514/712 |
| 4,992,475 | 2/1991 | Marcel | 514/718 |

FOREIGN PATENT DOCUMENTS

| | | | |
|---|---|---|---|
| 087161 | 2/1983 | European Pat. Off. | A61K 31/63 |
| 1 561 853 | of 1985 | France | A61K 31/10 |
| 24 17 671 | of 1971 | Germany | A61K 31/10 |
| 219385 | 3/1985 | Germany | A61K 53/72 |
| 2068952 | 2/1981 | United Kingdom | A61K 02/41 |
| 1151042 | of 1982 | United Kingdom | A61K 31/10 |
| WO-A-8 807856 | of 1980 | WIPO | A61K 31/10 |

OTHER PUBLICATIONS

W. Snipes et al., *Symp. of the Pharmacolo. Effects of Lipids, The Amer. Oil Chem. Soc.*, Champaign, Il., 1978, pp. 63–73, "Hydrophobic Alcohols and . . . Antiviral Agents".
D.Y.C. Fung et al., *Critical Review in Microbiology*, vol. 12 No. 2, 1985, pp. 153–183; "Effect of Phenolic Antioxidants on Microbial Growth".
J.E.F. Reynolds, "Martindale The Extra Pharmacopoeia" 29th edition, 1989, The Pharmaceutical Press, London, GB, p. 1203: "Probucol".
T. Oda et al., "Oxygen Radicals . . . Conjugated SOD," *Science* vol. 244, pp. 893–1016; May 26, 1989.
Wanda, P., et al., *Antimicrobial Agents and Chemotherapy* 10: 96(1976).
Keith, A.D., et al., *Proc. Soc. Expltl. Biol. & Med.* 170: 237 (1982).
Freeman, D.J., et al., *Clin. Pharmacol. Ther.* 38: 56 (1985).
Kim, K.S. et al., *J. Infec. Dis.* : 91 (1985).
Lane, et al., "Acquried Immunodeficiency Syndrome and Related Diseases" in Rose, et al. eds., *Manual of Clinical Laboratory Immonology*, 3d Ed., Am. Soc. Microbiol., pp. 582–586, 1986.
Oda, et al., *Science* 244: 974–976 (1989).
Aloia et al., PNAS 85: 900 (1988).
Hendler S., "The Oxygen Breakthrough," William Morrow and Company, Inc., New York, 1989.
Brugh, M., *Chemical Regulation of Immunity in Veterinary Med.*, A.R. Liss, 1984, pp. 229–234.
Brugh, M., *Science* 197: 1291 (1977).
Winston, et al., *Am. J. Vet. Res.* 41: 391 (1980).
Reimund, E., *Medical (HIV) Hypotheses* 23: 39 (1987).
Cupp, J., et al., *Antimicrobial Agents and Chemotherapy* 8: 698 (1975).
Pirtle, E.C. et al., *Am. J. Vet. Res.* 47: 1892 (1986).
Mar., J., *Advanced Organic Chemistry*, 3d ed., J. Wiley and Sons, 1985, pp. 360–362, 793–795.
T. Fujisawa, et al., *Synthesis* 39 (1973).
Snipes, et al., *Chem. Abst.* 82:149903x (1975).
Carew, et al., *Chem. Abst.* 108:16125d (1988).
Hendler, S., "The Complete Guide to Anti–Aging Nutrients," Simon and Schuster, New York, (1984).
Nara, et al., *Aids Res. and Human Retroviruses* 3: 283–302 (1987) (Mary Ann Liebert, Publ.).
Nara and Fischinger, *Nature* 332: 469–470 (1988).
H. Maeda, *Science News*, May 27, p. 325 (1989).
Hammerstedt, R.H., et al., *Biology of Reproduction* 14: 381–397 (1976).
Carew, T.E., et al., *PNAS USA* 84: 7725–7729 (1987).
Moldovanyi, et al., *Chem. Abst.* 109: 197191m (1988).
Hils, et al., *Chem Abst.* 106: 2733x (1987).

(List continued on next page.)

*Primary Examiner*—Russell Travers
*Attorney, Agent, or Firm*—Townsend & Townsend & Crew LLP

[57] ABSTRACT

This invention relates to compounds, compositions, uses and methods for inhibiting viral and retroviral replication and for treating viral and retroviral infections via the administration of various compounds, including antioxidants, preferably compounds corresponding to the formula

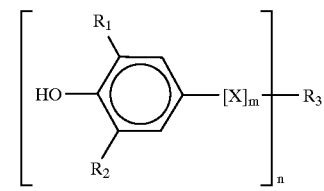

wherein n=1, 2, 3, or 4; m=0 or 1; X is O, S or $CH_2$; $R_1$ is hydrogen or tertiary butyl or lower alkyl of from one to six carbon atoms, inclusive; $R_2$ is tertiary butyl or lower alkyl of from one to six carbon atoms, inclusive; and $R_3$ is hydrogen or alkyl or aryl or mixed alkyl/aryl, containing a total of 5–25 carbon atoms.

9 Claims, 7 Drawing Sheets

OTHER PUBLICATIONS

Weuffen, et al., *Chem. Abst.* 103: 147169r (1985).
Prakash, et al., *Chem. Abst.* 96: 117404h (1982).
Kloecking, et al., *Chem. Abst.* 89: 158049v (1978).
Bydzovska, *Chem. Abst.* 85: 28509b (1976).
Drake, et al., *Chem. Abst.* 72: 20544v (1970).
Barnhart, et al., *Chem. Abst.* 73 646443b (1970).
Kritchevsky, et al., *Chem. Abst.* 74: 123504c (1971).
Kabara, et al., *Chem. Abst.* 88: 83965j (1978).
Prous, et al., *Chem. Abst.* 89: 16371v (1978).
Hoshide, et al., *Chem. Abst.* 93: 71280x (1980).
Hoshide, et al., *Chem. Abst.* 93: 94980q (1980).
Hoshide, et al., *Chem. Abst.* 93: 149970u (1980).
Ramos, et al., *Chem. Abst.* 95: 150171g (1981).
Mordasini, et al., *Chem. Abst.* 96: 79712x (1982).
DeMeglio, et al., *Chem. Abst.* 104: 28675p (1986).

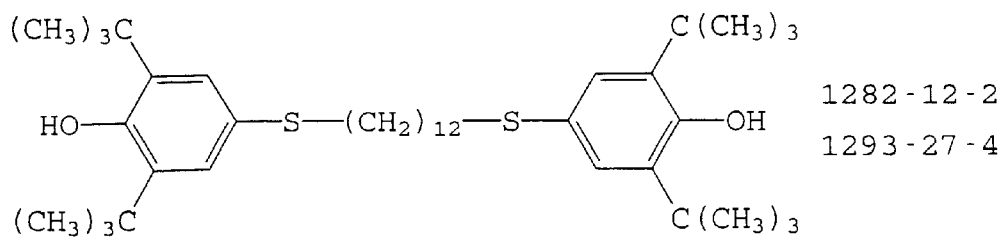
I
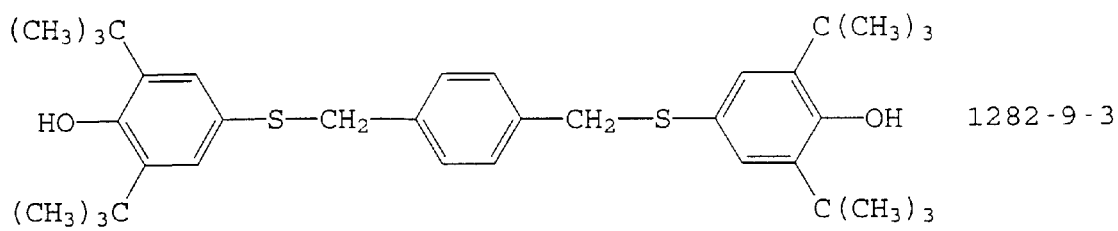
II
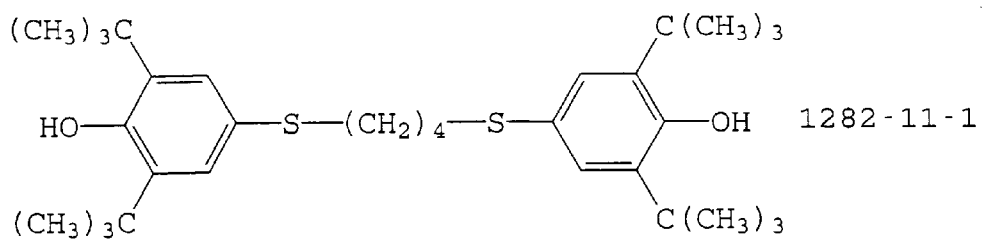
III
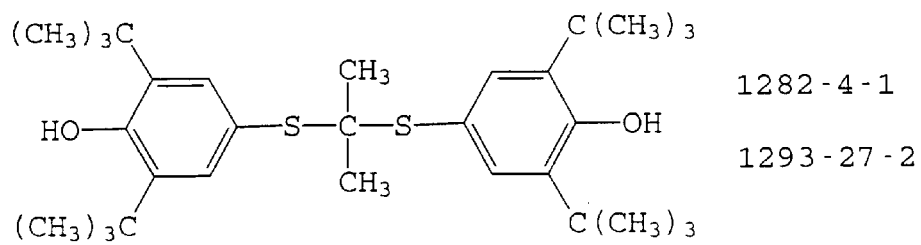
IV
FIGURE 1A

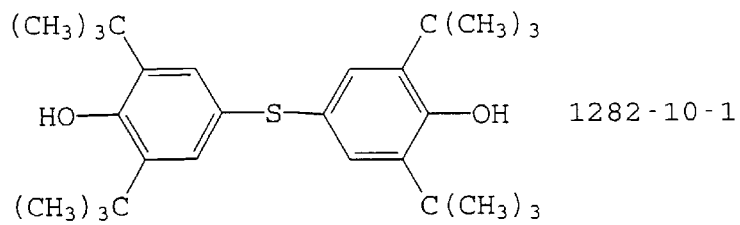
V
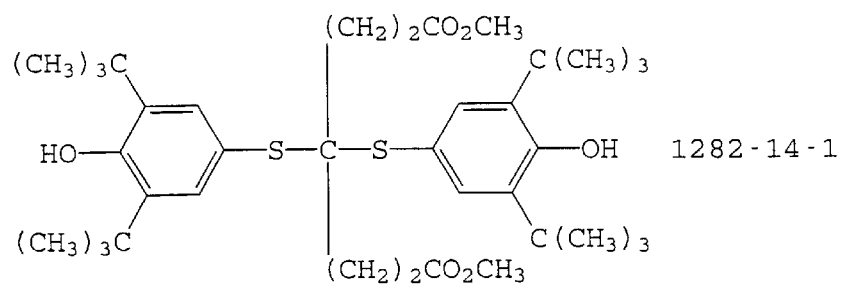
VI
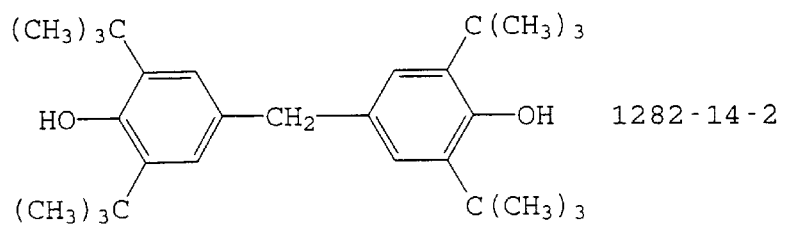
VII
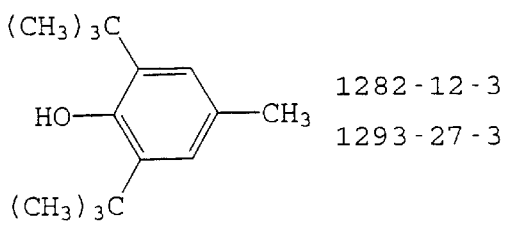
VIII
FIGURE 1B

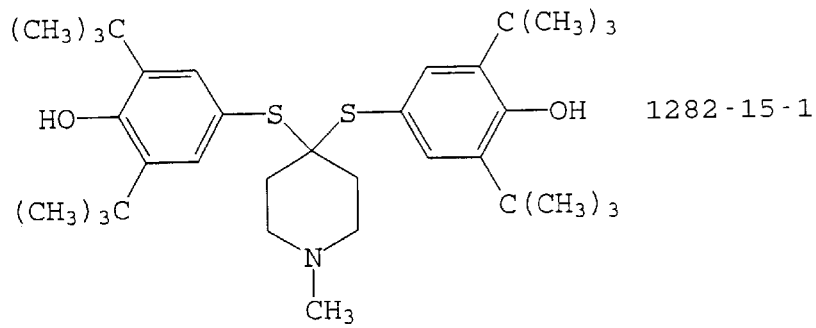
1282-15-1
IX
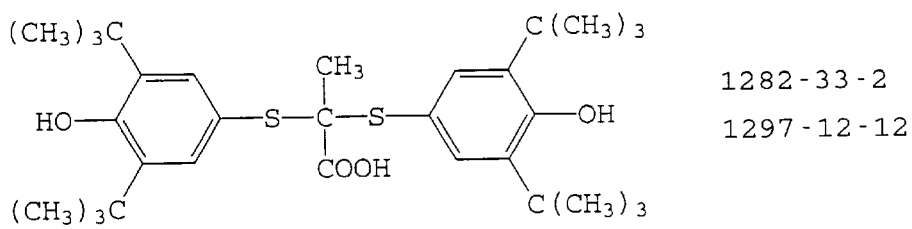
1282-33-2
1297-12-12
X
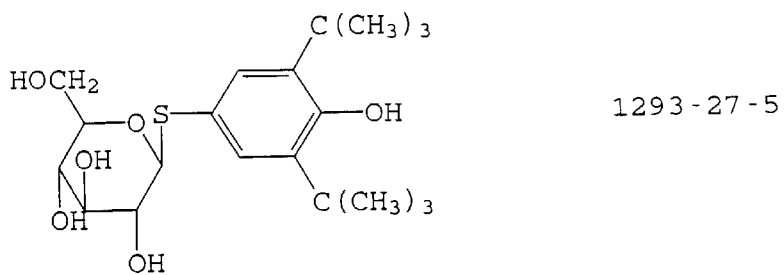
1293-27-5
XI
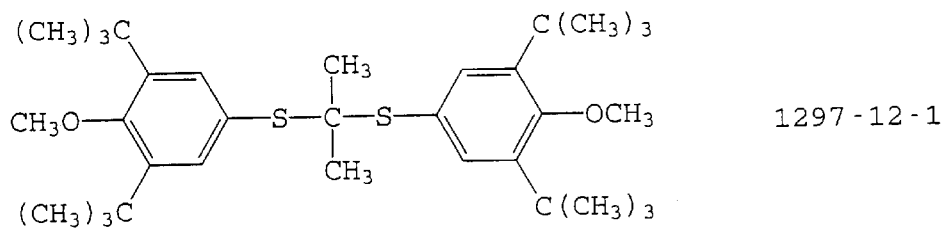
1297-12-1
XII
FIGURE 1C

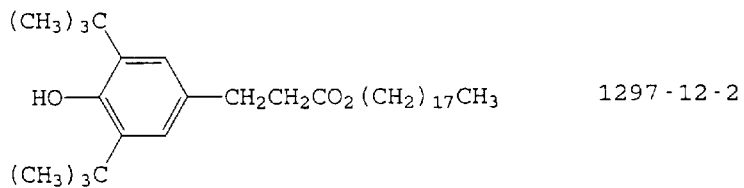
1297-12-2
XIII
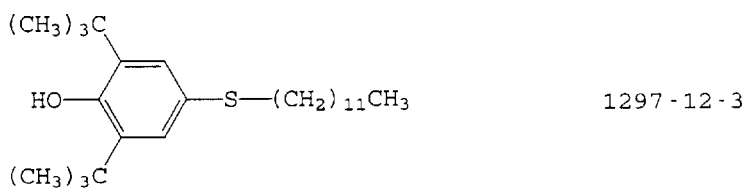
1297-12-3
XIV
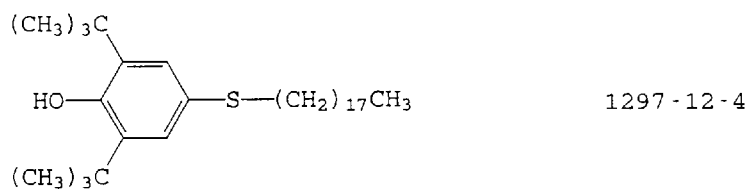
1297-12-4
XV
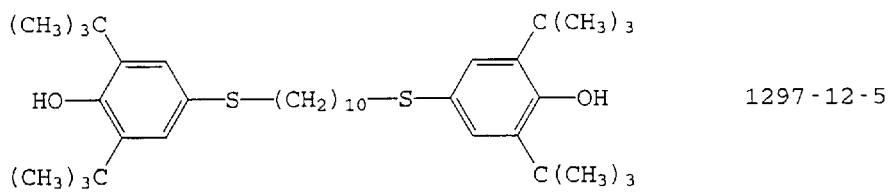
1297-12-5
XVI
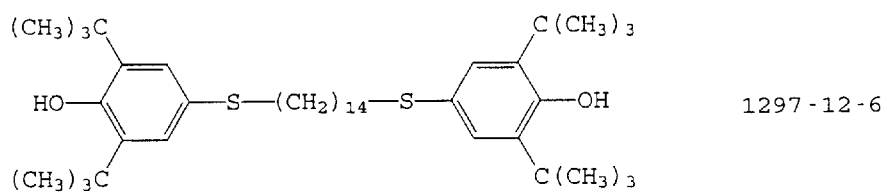
1297-12-6
XVII
FIGURE 1D

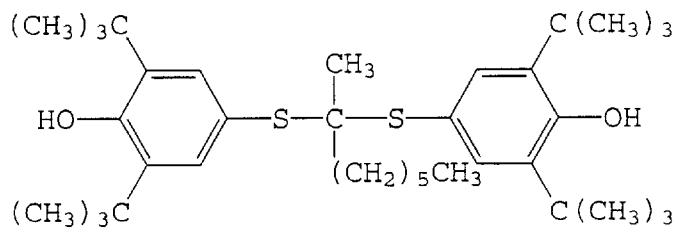
1297-12-7
XVIII
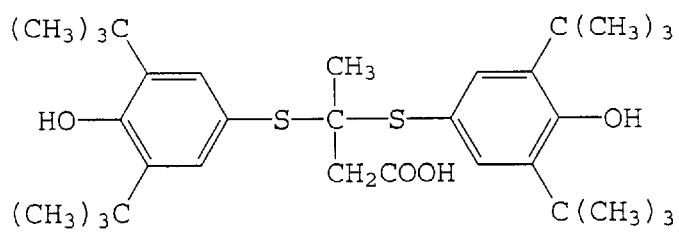
1297-12-8
XIX
FIGURE 1E

EFFECT OF DRUGS ON SYNCYTIAL CELL FORMATION (HIV-1/MOLT-3 SYSTEM): PERCENT REDUCTION OF SYNCYTIUM FORMATION

| | | Concentration of drug, ug/ml. | | | | | | |
|---|---|---|---|---|---|---|---|---|
| Drug | Test set | 30 | 10 | 3 | 1 | 0.3 | 0.1 | 0.01 | 0.001 |
| 1282-4-1 | 1A | 76 | 72 | 45 | 47 | --- | --- | --- | --- |
| 1282-9-3 | 2A | 91 | 86 | 88 | 68 | --- | --- | --- | --- |
| 1282-10-1 | 2B | 90 | 75 | 71 | 52 | --- | --- | --- | --- |
| 1282-11-1 | 1B | 73 | 62 | 49 | 55 | --- | --- | --- | --- |
| - | 4° | 94 | 83 | 84 | 81 | 85 | 78 | 50 | --- |
| 1282-12-2 | 2C | 76 | 86 | 78 | 64 | --- | --- | --- | --- |
| - | 4° | 82 | 79 | 8T | 80 | 68 | 61 | 32 | --- |
| 1282-12-3 | 1E | T | 79 | 76 | 69 | --- | --- | --- | --- |
| 1282-14-1 | 1C | 87 | 83 | 83 | 64 | --- | --- | --- | --- |
| 1282-14-2 | 1D | 87 | 72 | 53 | 46 | --- | --- | --- | --- |
| 1282-15-1 | 2E | T | T | 94 | 74 | --- | --- | --- | --- |
| 1282-33-2 | 2D | T | 83 | 69 | 40 | --- | --- | --- | --- |
| 1293-27-1 | 3 | 94 | 86 | 51 | 25 | --- | --- | --- | --- |
| " | 4 | 92 | 88 | 89 | 90 | 90 | 87 | 44 | --- |
| 1293-27-5 | 3 | 57 | 47 | 35 | 22 | --- | --- | --- | --- |
| " | 4° | 90 | 82 | 83 | 81 | 80 | 83 | 45 | --- |
| 1297-12-1 | 4A | T | T | 88 | 80 | 69 | 52 | --- | --- |
| " | 4° | 88 | 78 | 87 | 80 | 60 | 56 | --- | --- |
| 1297-12-2 | 4B | 58 | 54 | 54 | 65 | 50 | 51 | --- | --- |
| " | 4° | 69 | 68 | 71 | 70 | 57 | 54 | --- | --- |
| 1297-12-3 | 4C | 49 | 48 | 45 | 24 | 29 | 44 | --- | --- |
| " | 4° | 88 | 87 | 80 | 82 | 71 | 76 | 48 | --- |
| 1297-12-4 | 4D | 70 | 51 | 56 | 58 | 40 | 36 | --- | --- |
| " | 4° | 89 | 89 | 87 | 87 | 84 | 72 | 42 | --- |
| 1297-12-5 | 4E | 66 | 48 | 41 | 30 | 13 | 32 | --- | --- |
| " | 4° | 73 | 78 | 69 | 66 | 55 | 39 | 34 | --- |
| 1297-12-6 | 4F | 73 | 51 | 55 | 54 | 42 | 51 | --- | --- |
| " | 4° | 87 | 76 | 75 | 78 | 78 | 68 | 42 | --- |
| 1297-12-7 | 4G | 67 | 70 | 42 | 40 | 31 | 33 | --- | --- |
| " | 4° | 92 | 86 | 84 | 71 | 78 | 69 | 44 | --- |
| 1297-12-8 | 4H | T | 98 | 53 | 54 | 36 | 37 | --- | --- |
| " | 4° | 88 | 82 | 71 | 68 | 69 | 56 | 59 | --- |
| AZT | 1 | --- | --- | 100 | --- | 98 | --- | --- | --- |
| " | 2 | --- | --- | 82 | --- | 65 | --- | --- | --- |
| " | 3,4 | --- | 104 | --- | 100 | --- | 97 | --- | --- |
| " | 4° | --- | 96 | --- | 94 | --- | 90 | 85 | 76 |

T denotes toxic effect.
Sets 1 and 2 show the averaged values measured at days 2, 3 and 4.
Sets 3 and 4 show the averaged values measured at days 5, 6 and 7.
Set 4° shows the values measured at day

FIGURE 2

EFFECT OF DRUGS ON p24 LEVELS (HIV-1/MOLT-3 SYSTEM: p24 MEASURED BY ANTIGEN CAPTURE IMMUNOASSAY)

PERCENT REDUCTION OF P24 ANTIGEN

| Drug | Test set | \multicolumn{8}{c}{Concentration of drug, ug/ml} |
|---|---|---|---|---|---|---|---|---|---|

| Drug | Test set | 30 | 10 | 3 | 1 | 0.3 | 0.1 | 0.01 | 0.001 |
|---|---|---|---|---|---|---|---|---|---|
| 1282-4-1 | 1A | 93 | 82 | 36 | 16 | --- | --- | --- | --- |
| 1282-9-3 | 2A | 82 | 77 | 78 | 71 | --- | --- | --- | --- |
| 1282-10-1 | 2B | 93 | 76 | 92 | 60 | --- | --- | --- | --- |
| 1282-11-1 | 1B | 93 | 86 | 45 | 47 | --- | --- | --- | --- |
| 1282-12-2 | 2C | 49 | 63 | 92 | 91 | --- | --- | --- | --- |
| 1282-12-3 | 1E | T | 93 | 82 | 34 | --- | --- | --- | --- |
| 1282-14-1 | 1C | 88 | 91 | 88 | 25 | --- | --- | --- | --- |
| 1282-14-2 | 1D | 90 | 96 | 61 | 42 | --- | --- | --- | --- |
| 1282-15-1 | 2E | T | T | 89 | 85 | --- | --- | --- | --- |
| 1282-33-2 | 2D | T | 89 | 87 | 78 | --- | --- | --- | --- |
| 1293-27-1 | 3 | 75 | 51 | 34 | 32 | --- | --- | --- | --- |
| 1293-27-5 | 3 | 11 | 0 | 0 | 34 | --- | --- | --- | --- |
| 1297-12-1 | 4A | T | T | 63 | 57 | 35 | 16 | --- | --- |
| 1297-12-2 | 4B | 5 | 31 | 58 | 49 | 18 | 30 | --- | --- |
| 1297-12-3 | 4C | 42 | 13 | 18 | 28 | --- | 16 | --- | --- |
| 1297-12-4 | 4D | 42 | 14 | 49 | 62 | 57 | 30 | --- | --- |
| 1297-12-5 | 4E | 0 | 0 | 30 | 16 | 13 | 14 | --- | --- |
| 1297-12-6 | 4F | 30 | 9 | 25 | 42 | 22 | 28 | --- | --- |
| 1297-12-7 | 4G | 23 | 47 | 40 | 46 | 56 | 39 | --- | --- |
| 1297-12-8 | 4H | T | 64 | 45 | 55 | 46 | 51 | --- | --- |
| AZT | 1 | --- | --- | 99.99 | --- | 99.9 | --- | --- | --- |
| " | 2 | --- | --- | 92 | --- | 96 | --- | --- | --- |
| " | 3 | --- | 97 | --- | 97 | --- | 96 | --- | --- |
| " | 4 | --- | 92 | --- | 90 | --- | 91 | 96 | 74 |

T denotes toxic effect.
Sets 1 and 2 show the values measured at day 3.
Sets 3 and 4 show the averaged values measured at days 5, 6 and 7.

ANTIVIRAL AGENTS

This application is a continuation of U.S. patent application Ser. No. 08/130,168, filed Sep. 30, 1993, allowed, which is a continuation of Ser. No. 07/550,528, filed Jul. 10, 1990, abandoned, which is a CIP of Ser. No. 07/452,737 filed Dec. 19, 1989 abandoned, which is a CIP of Ser. No. 07/381,132, filed Jul. 14, 1989 issued as U.S. Pat. No. 4,985,465, Jan. 15, 1991, all of which are incorporated herein by reference.

BACKGROUND OF THE INVENTION

Diseases associated with viral and retroviral infections are major medical, veterinary and agricultural problems in the United States and worldwide. Diseases of known viral origin include chicken pox, the common cold, cytomegalovirus disease (CMV), dengue fever, encephalitis, hoof-and-mouth disease, herpes infections, influenza, keratoconjunctivitis, measles, mumps, Newcastle disease, poliomyelitis, rabies, rubella, scrapie, shingles, smallpox, tick fever, West Nile Fever, and yellow fever, to name but a few. An especially serious problem at the present time is the rapid escalation in reported cases of AIDS (Acquired Immune Deficiency Syndrome), whose causative agent is strongly suspected to be HIV (Human Immunodeficiency Virus).

There are urgent and compelling reasons for the development of more efficacious and safer treatments of viral and retroviral infections. It is estimated that at least one and a half million people in the United States alone have been infected with the human immunodeficiency (HIV) or AIDS virus. HIV causes a decay of a major arm of the immune system, the immune helper cells (T4 helper or $CD4^+$ helper cells). This decay leads to a wide spectrum of diseases, generally called HIV disease, of which AIDS is the most serious and devastating form. It is anticipated that over one third of the budget for medical care in the U.S. will be consumed on HIV disease. There is an escalating incidence of other viral diseases as well. For example, cytomegalovirus (CMV) infection is rapidly increasing in the teenage population of the United States.

We have noted that two commonly-used antioxidants and preservatives, butylated hydroxyanisole (BHA) and butylated hydroxytoluene (BHT) have been reported to have some efficacy in ameliorating some viral infections. Some of these reports are summarized below:

| VIRUS | REFERENCE |
|---|---|
| Newcastle Disease Virus | Brugh, M., "Chemical Regulation of Immunity", in Veterinary Med., A. R. Liss, 1984, pp. 229–234; Brugh, M., Science 197: 1291 (1977); Winston, et al., Am. J. Vet. Res. 41: 391 (1980). |
| HIV | Reimund, E., Medical (HIV) Hypotheses 23: 39 (1987); Aloia, et al., PNAS 85: 900 (1988). |
| Bacteriophage PM2 | Cupp, J., et al., Antimicrobial Agents and Chemotherapy 8: 698 (1975). |
| Pseudorabies Virus (PRV) | Pirtle, E. C., et al., Am. J. Vet. Res. 47: 1892 (1986). |
| Bacteriophage (φ6) | Wanda, P., et al., Antimicrobial Agents and Chemotherapy 10: 96 (1976). |
| Herpes Simplex Virus (HSV-1) | Keith, A. D., et al., Proc. Soc. Exptl. Biol. & Med. 170: 237 (1982). |
| Herpes Simplex Labialis (HSL) | Freeman, D. J., et al., Clin. Pharmacol. Ther. 38: 56 (1985). |
| Semliki Forest Virus (SFV) | Kim, K. S., et al., J. Infec. Dis. 138: 91 (1985). |
| Cytomegalovirus (CMV) | Kim, K. S., et al., J. Infec. Dis. 138: 91 (1985). |

It has been observed that certain viruses and retroviruses including, for example, cytomegalovirus (CMV), herpes simplex virus, herpes zoster virus, Epstein-Barr virus (EBV), Newcastle Disease virus, Semliki Forest virus, influenza viruses, pseudorabies virus, and human immunodeficiency virus (HIV), are of the lipid membrane variety. Further, we have hypothesized that BHT, BHA, and/or the compounds of the present invention may have some impact upon said membranes, albeit other mechanisms not presently known may be responsible for the unanticipated efficacy of the compounds of the present invention.

In addition, it has been theorized that free oxygen radicals may be involved in the pathogenesis of certain viral infections (see Oda, et al., Science 244: 974–976 (1989), and that antioxidants may have an impact upon viral or retroviral infections (see Hendler, S., "The Oxygen Breakthrough," William Morrow and Company, Inc., New York, 1989; or Hendler, S., "The Complete Guide to Anti-Aging Nutrients," Simon and Schuster, New York, 1984.)

As a result of our independent observations, we believe there might be substances possessing the ability to fluidize viral membranes, or otherwise affect their structures, in ways that make them less capable of infecting cells. It is to be expressly understood that the invention disclosed herein is not limited to or by a particular theory of operation, however.

In recent years, many investigators have proposed novel treatments for combating insidious forms of disease, many involving viruses or retroviruses as the causative agents. Due to the many differences that separate these pathogens—including, for example, their structure, their method of replication and their susceptibility to or resistance to various treatment modalities—one might not expect a single method of inhibiting the development of viral and retroviral infections o be feasible. Nevertheless, such a methodology is now available, due to the unanticipated efficacy of known and novel compounds in affecting membrane fluidity, among other things.

Therefore, in response to this pervasive need for safer and more efficacious treatments of viral and retroviral infections, and in light of our observations, we undertook to design and synthesize a variety of new molecules and to propose methods for their use, in order to further explore the relationship of structure and activity, in the hope of discovering even more highly effective antiviral substances.

The present invention also relates to methods for inhibiting viral and retroviral infections via use of known compounds with unexpected efficacy in combating viral and retroviral infections. The present invention also suggests the use of novel compounds to inhibit these infections, as well as methods for their use in living organisms.

SUMMARY OF THE INVENTION

Ideally, one type of substance that could conceivably affect the infectivity of a viral or retroviral agent should have some or all of the following characteristics: a) solubility in lipid membranes, with preferential solubility in the lipid membranes of viruses as opposed to the cells of the body of the host; b) ability to extract cholesterol from viral membranes; c) antioxidant ability to prevent lipid peroxidation; d) easy absorbability into the body; e) the ability to penetrate the blood-brain barrier; and f) a very high therapeutic-to-toxicity index. It is anticipated that all membraned viruses, including herpes simplex, herpes zoster, CMV, EBV, influenza viruses, and the human immunodeficiency viruses may be inhibited to some extent by such substances at doses that will not produce toxic side effects. In addition, it is also anticipated that the within invention may be successfully applied to viruses and retrovirus which lack envelopes, including the DNA and RNA viruses. The invention disclosed within is not limited to or by a particular theory of operation, however. It is simply suggested that the observed efficacy of compositions suggested by the present disclosure may be due, at least in part, to the characteristics noted above.

This invention relates to novel compositions and methods for using same for inhibiting viral and retroviral infections. In particular, the use of sterically hindered phenolic antioxidants is suggested. Even more particularly, the invention is directed to methods for using novel pharmaceutical compositions to inhibit viral and retroviral infections in vivo wherein the compositions comprise an effective amount of a bis(dialkylphenol) mercaptal or a bis(dialkylphenol) mercaptole compound.

One candidate substance which proved to have unexpectedly promising antiviral activity in this regard is the drug probucol, which is obtainable under the name Lorelco (Merrell Dow Pharmaceuticals, Inc.). Methods for utilizing this particular compound in lowering serum cholesterol are set forth in U.S. Pat. No. 3,862,332, which is incorporated herein by reference.

Therefore, one embodiment of the present invention discloses a method for inhibiting viral and retroviral infections or for inhibiting viral and retroviral replication in living organisms comprising administering to living organisms an effective amount of a compound, or a composition containing a compound, corresponding to the formula

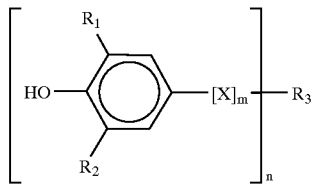

wherein n=1, 2, 3, or 4; wherein m=0 or 1; wherein X represents O, S or $CH_2$; wherein $R_1$ represents hydrogen or tertiary butyl or lower alkyl of from one to six carbon atoms, inclusive; wherein $R_2$ represents tertiary butyl or lower alkyl of from one to six carbon atoms, inclusive; and wherein $R_3$ represents hydrogen or alkyl or aryl or mixed alkyl/aryl, containing a total of 5–25 carbon atoms. In a preferred embodiment, $R_1$ and $R_2$ represent tertiary butyl.

The present embodiment additionally discloses a method for inhibiting viral and retroviral infections in living organisms comprising administering to a living organism an effective amount of an antioxidant compound. In one embodiment of the present invention, the antioxidant compound may also be sterically hindered; in another preferred embodiment, the compound is also phenolic.

In one preferred embodiment, the compounds disclosed herein are incorporated in a pharmaceutically acceptable carrier or excipient. Preferred methods of administering the compounds of the present invention include parenteral, oral, intraperitoneal, transdermal and topical administration, as well as administration via inhalation.

It is thus one object of this invention to provide methods for using novel compounds or pharmaceutical compositions to inhibit viral and retroviral infections, by administering them to living organisms, including plants and animals. A further object of this invention is to provide a novel method for treating viral and retroviral infections in living organisms. Another object of the present invention is to provide a novel method for inhibiting viral and retroviral replication in living organisms. Yet another object of the invention is to provide novel uses for compositions which have the ability to inhibit viral and retroviral replication in living organisms, and which have low toxicity at dosage levels consistent with their indicated activity. A further object of this invention is to suggest methods for the alleviation of viral and retroviral infections in a variety of organisms, including plants, animals, and more particularly, in mammals, including humans.

The present invention also discloses methods for treating viral and retroviral infections or for inhibiting viral and retroviral replication in living organisms comprising administering to living organisms an effective antiviral amount of the aforementioned compounds.

In one embodiment of the present invention, the compound used according to the disclosed method has antioxidant properties; in another embodiment, it may also be phenolic; in yet another embodiment, the compound may be a sterically hindered phenol.

Another aspect of the invention is a composition useful in the treatment of viral and retroviral infections or for inhibiting viral and retroviral replication in living organisms comprising an effective antiviral amount of a compound corresponding to the formula

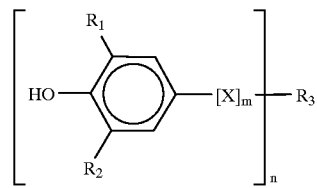

wherein n=1, 2, 3, or 4, wherein m=0 or 1, wherein X represents O, S or $CH_2$, wherein $R_1$ represents hydrogen or tertiary butyl or lower alkyl of from one to six carbon atoms, inclusive, $R_2$ represents tertiary butyl or lower alkyl of from one to six carbon atoms, inclusive, and wherein $R_3$ represents hydrogen or alkyl or aryl or mixed alkyl/aryl, containing a total of 5–25 carbon atoms. In a preferred embodiment, $R_1$ and $R_2$ represent tertiary butyl.

Examples of compounds that may be utilized according to the disclosed embodiments include bis(3,5-di-tert-butyl-4-hydroxyphenyl) acetone mercaptole, bis(3,5-di-tert-butyl-4-hydroxyphenyl) butanone mercaptole; bis(3-tert-butyl-4-hydroxy-5-isopropylphenyl) acetone mercaptole; bis(3-tert-butyl-4-hydroxy-5-methylphenyl) acetone mercaptole; 1,12-di(3,5-di-tert-butyl-4-hydroxyphenylthio)dodecane; α,α'-di(3,5-di-tert-butyl-4-hydroxyphenylthio)-p-xylene; 1,4-di(3,5-di-tert-butyl-4-hydroxyphenlythio)butane; acetone bis(3,5-di-tert-butyl-4-hydroxyphenyl) mercaptole ("probucol"); bis (3,5-di-tert-butyl-4-hydroxyphenyl) sulfide; dimethyl gamma-ketopimelate bis(3,5-di-tert-butyl-4-hydroxyphenyl) mercaptole; 2,6-di-tert-butyl-4-methylphenol (BHT); 4,4'-thiobis(6-tert-butyl-o-cresol), 1,3,5-trimethyl-2,4,6-tris(3,5-di-tert-butyl-4-hydroxybenzyl) benzene; and 4,4'-methylenebis(2,6-di-tert-butylphenol).

Other examples include 3,5-di-t-butyl-4-hydroxyphenyl β-D-thioglucopyranoside; bis(3,5-di-t-butyl-4-methoxyphenyl) mercaptole; 2,6-di-t-butyl-4-(dodecylthio) phenol; 2,6-di-t-butyl-4-(octadecylthio) phenol; 1,10-di(3,5-di-t-butyl-4-hydroxyphenylthio)decane; 1,14-di(3,5-di-t-butyl-4-hydroxyphenylthio)tetradecane; 2-octanone bis(3,5-di-t-butyl-4-hydroxyphenyl)mercaptole; acetoacetic acid bis (3,5-di-t-butyl-4-hydroxyphenyl) mercaptole; 2,6-di-tert-butyl- -dimethylamino-p-cresol; 1,3,5-trimethyl-2,4,6-tris (3,5-di-tert-butyl-4-hydroxybenzyl)-benzene ("Ethanox₁ 330"); octadecyl 3,5-di-tert-butyl-4-hydroxyhydrocinnamate ("Ethanox₁ 376"); 6-tert-butyl-2,4-dimethylphenol ("Ralox₁624"); tetrakis [methylene(3,5-di-tert-butyl-4-hydroxyhydrocinnamate)] methane ("Ralox$_{S1}$ 630"); 2,2'-methylene-bis(4-methyl-6-tert-butylphenol) ("Ralox₁ 2246"); tert-butylhydroquinone ("Tenox₁ TBHQ"); 2,6-dicyclohexyl-p-cresol (Ethyl Corporation, Baton Rouge, La.); bis(3,5-di-tert-butyl-4-hydroxyphenyl) methane ("Ethanox₁ 702"); and methylene bridged polyalkyl phenols, comprising 4,4'-methylenebis(2,6-di-tert-butylphenol), solvents, and alkylated phenols, principally 2,4,6 tri-tert-butylphenol ("Ethanox₁ 728"). (Ethanox₁ is a registered trademark of Ethyl Corporation; Ralox₁ is a registered trademark of Raschig AG, Ludwigshafen, Germany; and Tenox₁ is a registered trademark of Eastman Chemical Products, Kingsport, Tenn.)

In one preferred embodiment, the compounds disclosed herein are incorporated in a pharmaceutically acceptable carrier or excipient. Preferred methods of administering the compounds of the present invention include parenteral, oral, intraperitoneal, transdermal, topical, and liposomal administration, as well as administration via inhalation.

In particular preferred embodiments of the composition, the active ingredient compound is phenolic; in yet another embodiment, the compound may be a sterically hindered phenol. Other examples of preferred compositions comprise effective antiviral amounts of a compound according to the above formula; examples of appropriate compounds have been noted above.

In other embodiments, the compound is incorporated in a pharmaceutically acceptable carrier or excipient. In various alternative embodiments, the composition may be administered parenterally, orally, intraperitoneally, topically, transdermally, via inhalation, or liposomally.

In various alternative embodiments, methods for treating viral or retroviral infections in a living organism comprising administering to a living organism an effective antiviral amount of any of the disclosed compounds are suggested. The present invention also discloses methods for inhibiting viral or retroviral replication in a living organism comprising administering an effective antiviral amount of any of the disclosed compounds. In various embodiments of these methods, the compound may be administered parenterally, orally, intraperitoneally, topically, transdermally, via inhalation, or liposomally. Further, the methods are useful for the treatment of plants or animals, including mammals, and humans in particular.

The present embodiment additionally discloses a composition useful in the treatment of viral and retroviral infections in living organisms, comprising an effective antiviral amount of an antioxidant compound incorporated in a pharmaceutically acceptable carrier or excipient. The present invention also discloses a method for inhibiting viral and retroviral replication and/or infections in living organisms comprising administering a composition comprising an effective antiviral amount of an antioxidant compound incorporated in a pharmaceutically acceptable carrier or excipient to a living organism.

Whether used to inhibit viral replication or to treat viral infections, other embodiments disclose that, for administration to plants, the compounds are preferably dissolved or dispersed in a liquid medium (e.g., in an oil, or in an aqueous solvent with the aid of a detergent or other dispersant) at a concentration in the range of about 0.001% to 1%, and applied by spraying or sprinkling. For administration to animals, including mammals, the dosage units of the compositions would preferably fall within the range of about 1 mg per kg of body weight, to about 100 mg/kg, with a range of about 2 mg/kg to about 80 mg/kg being even more preferred.

BRIEF DESCRIPTION OF THE DRAWINGS

FIG. 1 diagrams the chemical structure and labels used for some of the compounds of the present invention.

FIG. 2 diagrams the chemical structure and labels used for some of the compounds of the present invention.

FIG. 3 illustrates the results of tests measuring the effect of the compounds of the present invention on syncytial cell formation.

FIG. 4 illustrates the results of tests measuring the effect of the compounds of the present invention on p24 antigen levels.

DETAILED DESCRIPTION

We have observed that the membrane fluidity or other properties of viral and retroviral agents may be disturbed and affected by adminstration of substituted compounds, or compositions or dosage unit forms, such compounds corresponding to the following formula:

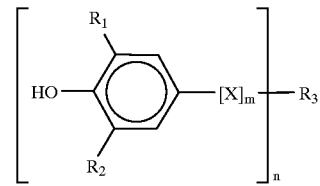

In the present specification and claims, n=1, 2, 3, or 4; m=0 or 1; X represents O, S, $CH_2$, or $R_3$; $R_1$ represents hydrogen or tertiary butyl or lower alkyl of from one to six carbon atoms, inclusive; $R_2$ represents tertiary butyl or lower alkyl of from one to six carbon atoms, inclusive; and $R_3$ represents hydrogen or alkyl or aryl or mixed alkyl/aryl, containing a total of 5–25 carbon atoms.

A particularly preferred group of compounds for use in the practice of the invention comprises non-ionic compounds corresponding to the above formula. These compounds can be prepared as disclosed infra. For the sake of convenience, compounds having the above-described chemical structures will be referred to hereinafter as "BHT derivatives", or they may also collectively be referred to herein as "antioxidants".

Other examples include S,S'-di-substituted mercaptals of an aldehyde or an S,S'-di-substituted mercaptole of a ketone containing from two to twenty carbon atoms, inclusive, wherein the substituents are 3-tertiary-alkyl-4-hydroxy-5-lower alkyl phenyl groups in which the tertiary alkyl groups are tertiary butyl groups and the lower alkyl groups are methyl, ethyl, propyl or butyl.

One particular aspect of the invention comprises administration of sterically hindered phenolic antioxidants, such compounds corresponding to derivatives of butylated hydroxytoluene (BHT), said derivatives comprising conjugates of from about one to four modified BHT moieties. Examples of such compounds include the following Ethanox® compounds, which are commercially available from Ethyl Corporation (Baton Rouge, La.): 1,3,5-trimethyl-2,4,6-tris(3,5-di-tert-butyl-4-hydroxybenzyl)-benzene ("Ethanox® 330"); octadecyl 3,5-di-tert-butyl-4-hydroxyhydrocinnamate ("Ethanox® 376"); 4,4,'-§methylenebis(2,6-di-tert-butylphenol) ("Ethanox® 702"); "Ethanox® 728", which is comprised of about 80 wt % methylene bridged polyalkyl phenols, over 50% of which comprises 4,4'-methylenebis(2,6-di-tert-butylphenol), about 5 wt % solvents, and about 15 wt % alkylated phenols, principally 2,4,6 tri-tert-butylphenol; 1,3,5-trimethyl-2,4,6-tris(3,5-di-tert-butyl-4-hydroxybenzyl)-benzene ("Ethanox® 330"); and octadecyl 3,5-di-tert-butyl-4-hydroxyhydrocinnamate ("Ethanox® 376").

Examples of other effective antiviral antioxidants include: 6-tert-butyl-2,4-dimethylphenol ("Ralox® 624"); tetrakis [methylene(3,5-di-tert-butyl-4-hydroxyhydrocinnamate)] methane ("Ralox® 630"); 2,2'-methylene-bis(4-methyl-6-tert-butylphenol) ("Ralox® 2246"); tert-butylhydroquinone ("Tenox® TBHQ"); and 2,6-dicyclohexyl-p-cresol (Ethyl Corporation, Baton Rouge, La.).

The above-referenced compounds can be administered topically, orally or parenterally by subcutaneous, intramuscular, intravenous or intraperitoneal injection or by implantation or the like, oral administration being preferred. The antioxidant compounds, including BHT derivatives, are preferably administered as pharmaceutical compositions in dosage unit form. Such compositions can be prepared by known techniques, for example, tableting or encapsulation. For administration to humans, the dosage units of the antioxidants, including BHT derivatives, preferably contain from about 100, 200, or 500 milligrams (mg) to about one or five grams of the active ingredient. Dosage units, adapted for oral administration, such as liquids, tablets, capsules, lozenges, and the like, may contain up to about five grams of active ingredient, albeit they preferably contain from about 100 to about 500 mg of the active ingredient, for ease of administration. The compounds can also be administered as compositions adapted to be fed as part or all of the organism's diet.

For administration to plants, the compounds are preferably dissolved or dispersed in a liquid medium (e.g., in an oil, or in an aqueous solvent with the aid of a detergent or other dispersant) at a concentration in the range of about 0.001% to 1%, and applied by spraying or sprinkling. For administration to animals, including mammals, the dosage units of the compositions would preferably fall within the range of about 1 mg per kg of body weight, to about 100 mg/kg, with a range of about 2 mg/kg to about 80 mg/kg being even more preferred.

In forming the compositions of the present invention, the active compound is incorporated in a pharmaceutical carrier. In the present specification and claims, the term "pharmaceutical carrier" refers to pharmaceutical excipients and includes nutritive compositions such as solid or liquid foodstuff. In the present specification and claims, "pharmaceutical excipient" refers to known pharmaceutical excipients which are substantially non-toxic and non-sensitizing at dosages consistent with their desired activity, e.g., with cholesterol reducing activity, in the case of probucol. A preferred pharmaceutical carrier is, for example, a surface-active dispersing agent or a liposomal carrier.

Suitable solid pharmaceutical carriers which can be employed for formulating the compositions of the invention include starch, lactose, glucose, sucrose, gelatin, microcrystalline cellulose, powdered licorice, powdered tragacanth, malt, rice flour, silica gel, magnesium stearate, magnesium carbonate, hydroxypropyl methyl cellulose, chalk and the like, and compatible mixtures thereof. In the preparation of solid compositions, the active ingredient can be triturated with a solid pharmaceutical carrier or mixtures thereof, or otherwise mechanically milled to obtain a uniform mixture. The mixtures can be compressed into tablets or filled into capsules by known procedures, or they can be employed as powders or the like. The solid compositions generally contain from about 0.02 to about 90 percent by weight, inclusive, of the active ingredient, although neat dosages are also contemplated.

Among the liquid pharmaceutical carriers which can be utilized are ethyl alcohol, propylene glycol, polyethylene glycols, peanut oil, corn oil, water, saline solution, liposomes, glycerides, glycerine and water mixtures, glucose syrup, syrup of acacia, mucilage of tragacanth and the like, and compatible mixtures thereof.

The compounds of the present invention may be administered in various efficacious amounts. The preferred dosage range of active ingredient for adult humans is from about 0.25 grams (gm) to about 5 gm per day, with a range of 0.5 gm to 2 gm per day being somewhat more preferable. The active ingredient may be administered topically, transdermally, orally, parenterally (e.g., subcutaneously, intravenously or intramuscularly), intraperitoneally, or via inhalation.

The membrane fluidity or other properties of viral and retroviral agents may also be disturbed via administration of a substituted compound, or a composition or dosage unit form, being an S,S'-di-substituted mercaptal of an aldehyde or an S,S'-di-substituted mercaptole of a ketone containing from two to twenty carbon atoms, inclusive, wherein the substituents are 3-tertiary-alkyl-4-hydroxy-5-lower alkyl phenyl groups in which the tertiary alkyl groups are tertiary butyl groups and the lower alkyl groups are methyl, ethyl, propyl or butyl. A particularly preferred group of compounds for use in the practice of the invention comprises the bis(3-tert-butyl-4-hydroxy-5-lower alkylphenyl) ketone mercaptoles corresponding to the above formula. Another preferred group comprises the bis(3,5-di-tert-butyl-4-hydroxyphenyl) ketone mercaptole compounds of the above formula, the compound bis(3,5-di-tert-butyl-4-hydroxyphenyl) acetone mercaptole being particularly preferred for use in the composition and method of the invention. These compounds can be prepared as disclosed in U.S. Pat. No. 3,862,332.

For the sake of convenience, compounds having the above-described chemical structures may be referred to hereinafter as "substituted ketone mercaptole" compounds. It is to be understood that these compounds may also function as antioxidants.

The above-referenced compounds can be administered topically, orally or parenterally by subcutaneous, intramuscular, intravenous or intraperitoneal injection or by implantation or the like, oral administration being preferred. The antioxidant compounds, including substituted ketone mercaptole compounds, are preferably administered as pharmaceutical compositions in dosage unit form. Such compositions can be prepared by known techniques, for example, tableting or encapsulation. The dosage units of the antioxidants, including the substituted mercaptole compounds, preferably contain from about 100 to about 200 to about 500 milligrams (mg) to about one to about five grams of the active ingredient. Dosage units, adapted for oral administration, such as tablets, capsules, lozenges, and the like, may contain up to about five grams of active ingredient, albeit they preferably contain from about 100 to about 500 mg of the active ingredient, for ease of administration. The compounds can also be administered as compositions adapted to be fed as part or all of the organism's diet.

In forming the compositions of the present invention, the active compound is incorporated in a pharmaceutical carrier. In the present specification and claims, the term "pharmaceutical carrier" refers to pharmaceutical excipients and includes nutritive compositions such as solid or liquid foodstuff. In the present specification and claims, "pharmaceutical excipient" refers to known pharmaceutical excipients which are substantially non-toxic and non-sensitizing at dosages consistent with their desired activity, e.g., with cholesterol reducing activity, in the case of probucol. A preferred pharmaceutical carrier is, for example, a surface-active dispersing agent.

Suitable solid pharmaceutical carriers which can be employed for formulating the compositions of the invention include starch, lactose, glucose, sucrose, gelatin, microcrystalline cellulose, powdered licorice, powdered tragacanth, malt, rice flour, silica gel, magnesium stearate, magnesium carbonate, hydroxypropyl methyl cellulose, chalk and the like, and compatible mixtures thereof. In the preparation of solid compositions, the active ingredient can be triturated with a solid pharmaceutical carrier or mixtures thereof, or otherwise mechanically milled to obtain a uniform mixture. The mixtures can be compressed into tablets or filled into capsules by known procedures, or they can be employed as powders or the like. The solid compositions generally contain from about 0.02 to about 90 percent by weight, inclusive, of the active ingredient, although neat dosages are also contemplated.

Among the liquid pharmaceutical carriers which can be utilized are ethyl alcohol, propylene glycol, polyethylene glycols, peanut oil, corn oil, water, saline solution, liposomes, glycerides, glycerine and water mixtures, glucose syrup, syrup of acacia, mucilage of tragacanth and the like, and compatible mixtures thereof.

The compounds of the present invention may be administered in various efficacious amounts. The preferred dosage range of active ingredient is from about 0.25 grams (gm) to about 5 gm per day, with a range of 0.5 gm to 2 gm per day being somewhat more preferable. The active ingredient may be administered topically, transdermally, orally, parenterally (e.g., subcutaneously, intravenously or intramuscularly), intraperitoneally, or via inhalation.

The invention can be better understood by way of the following examples which are representative of the preferred embodiments thereof, but which are not to be construed as limiting the scope of the invention.

EXAMPLE I

Synthesis of Analogs

The purity of each compound was confirmed by melting points and by thin layer chromatography. The structure of each compound was confirmed by nuclear magnetic resonance (NMR) spectroscopy. The compounds referred to below are illustrated in FIGS. 1 and 2.

I, II, III:

These compounds were prepared by standard methods of synthesis of thioethers, via displacement of halide ion from an alkyl halide with a thiophenolate nucleophile. (See, for example, March, J., *Advanced Organic Chemistry*, 3d ed., J. Wiley and Sons, 1985, pp. 360–362.) Thus 2,6-di-tert-butyl-4-mercaptophenol was reacted with 1,12-dibromododecane (for I), p-xylylene dibromide (for II), or 1,4-dibromobutane (for III), in N,N-dimethylformamide in the presence of powdered potassium carbonate. The products were washed free of solvents and salts with water and purified by recrystallization from organic solvents.

Compound I had the appearance of white crystals from isopropyl alcohol, with a melting point between 74–75° C. Compound II appeared as white crystals from isopropyl alcohol, with a melting point between 159–161° C. Compound III appeared as white crystals from isopropyl alcohol, with a melting point between 143–145° C.

IV, VI, IX, X;

These ketone mercaptoles were prepared by standard methods of synthesis in which a thiophenol is condensed with a ketone under acid catalysis in an organic solvent (see, e.g., March, J., *Advanced Organic Chemistry*, 3d ed., J. Wiley & Sons, 1985, pp. 793–795). Thus, 2,6-di-t-butyl-4-mercaptophenol was reacted with acetone (for IV), dimethyl gamma-ketopimelate (for VI), N-methyl-4-piperidone (for IX), or methyl pyruvate (for X, methyl ester) and the products were purified by recrystallization from organic solvents.

Compound IV appeared as white crystals from ethanol, melting point 125–126° C. Compound VI appeared as white crystals from isopropyl alcohol, melting point 152–154° C. Compound IX appeared as white crystals from isopropyl alcohol, melting point 254–256° C. Compound X, methyl ester, appeared as white crystals from isopropyl alcohol with a melting point of 111–113° C.

With respect to Compound X, the free acid was prepared from the methyl ester by saponification with sodium hydroxide, followed by acidification with HCl. White crystals were obtained and purified by crystallization from hexane, said crystals having a melting point of 151–153° C.

Compound V was synthesized by the method of T. Fujisawa, et al., *Synthesis* 39 (1973). Yellow crystals were obtained after crystallization from benzene/toluene, and had a melting point of about 137–138° C.

Additional analogs labeled XI-XIX (and further identified with "test code" nos., e.g., 1293-27-5), such as those diagrammed in FIG. 2, were prepared as described above, except for those obtained from various identified sources. As noted earlier, the Ethanox® compounds may be obtained from Ethyl Corporation, Baton Rouge, La.; Ralox® is obtainable from Raschig AG, Ludwigshafen, Germany; and Tenox® may be obtained from Eastman Chemical Products, Kingsport, Tenn.)

Analogs XI–XIX may be further identified as follows:

XI: 3,5-di-t-butyl-4-hydroxyphenyl β-D-thioglucopyranoside;

XII: bis(3,5-di-t-butyl-4-methoxyphenyl) mercaptole;

XIII: octadecyl 3,5-di-t-butyl-4-hydroxyhydrocinnamate (Ethanox® 330);

XIV: 2,6-di-t-butyl-4-(dodecylthio)phenol;

XV: 2,6-di-t-butyl-4-(octadecylthio)phenol;

XVI: 1,10-di(3,5-di-t-butyl-4-hydroxyphenylthio)decane;

XVII: 1,14-di(3,5-di-t-butyl-4-hydroxyphenylthio) tetradecane;

XVIII: 2-octanone bis(3,5-di-t-butyl-4-hydroxyphenyl) mercaptole;

XIX: acetoacetic acid bis(3,5-di-t-butyl-4-hydroxyphenyl) mercaptole.

EXAMPLE II

In Vitro Inhibition Tests

The following compounds were tested for their ability to inhibit HIV-1 virus infection in vitro. The compounds tested were: 1) 1,12-di(3,5-di-tert-butyl-4-hydroxyphenylthio) dodecane; 2) α,α'-di(3,5-di-tert-butyl-4-hydroxyphenylthio)-p-xylene; 3) 1,4-di(3,5-di-tert-butyl-4-hydroxyphenlythio)butane; 4) acetone bis(3,5-di-tert-butyl-4-hydroxyphenyl) mercaptol ("probucol"); 5) bis (3,5-di-tert-butyl-4-hydroxyphenyl) sulfide: 6) dimethyl gamma-ketopimelate bis(3,5-di-tert-butyl-4-hydroxyphenyl) mercaptole; 7) bis(3,5-di-tert-butyl-4-hydroxyphenyl) methane; 8) 2,6-di-tert-butyl-4-methylphenol) (BHT); 9) N-methyl-4-piperidone bis(3,5-di-tert-butyl-4-hydroxyphenyl) mercaptole; and 10) pyruvic acid bis (3,5-di-tert-butyl-4-hydroxyphenyl) mercaptole.

Preparation of Test Solutions

The stock solutions of the compounds consisted of DMSO (dimethyl sulfoxide) containing from 1% to 3% w/v of the compound. These stock solutions were diluted into the aqueous test media as needed to achieve the desired final concentration. An additional control in each test set contained DMSO only. The concentrations tested were as follows:

1) 300 µg/ml (1%–3% DMSO);
2) 100 µg/ml (1% DMSO);
3) 30 µg/ml (dilute in medium containing 1% DMSO);
4) 10 µq/ml (dilute in medium containing 1% DMSO);
5) 3 µg/ml (dilute in medium containing 1% DMSO);
6) 1 µg/ml (dilute in medium containing 1% DMSO).

The controls included: 1) 3% DMSO, uninfected; 2) 1% DMSO, uninfected; 3) no DMSO, uninfected; 4) AZT 10 µM, 1% DMSO; 5) AZT 1 µM, 1% DMSO; 6) No drug, infected, 3% DMSO; and 7) no drug, infected, 1% DMSO.

Testing Protocol

Prepare 15 ml of each of the media at the indicated concentrations of compound and/or solvent. A washed pellet consisting of $1.5 \times 10^6$ cells of Molt-3 (a clonal derivative of a lymphocyte (T-cell) line of Japanese origin, obtained from the National Institutes of Health, Bethesda, Md.) was suspended in 1 ml of each compound or control medium. Each tube was incubated with occasional shaking at 37° for four hours.

During the last hour of the preincubation period, Molt-3 grown HIV-1 was diluted into 1 ml each of the media to provide 200 $TCID_{50}$ units. Polybrene (10 µg/ml) was included in each tube.

The cells were pelleted and resuspended in the virus-containing media, then incubated for 60 minutes at 37° with occasional shaking. The cells were then pelleted and resuspended in 5 ml of each medium. Each cell pellet was washed twice in complete growth medium, then transferred to labeled 6-well trays.

On a daily basis, giant cells and syncytia were counted. At the same time, 0.5 ml of the culture was removed and frozen at −70° C. Fresh medium was used for replenishment.

At the end of three days, antigen capture analysis by immunoassay was performed. At the end of a 4–5 day period, uninfected cells were tested for viability by Trypan Blue exclusion.

Results

Screening of Drugs in the Molt-3/HIV 1 Assay System

| Cmpd (Drug) | 50% reduction in syncytium formation | 50% reduction in p24 antigen | 50% kill of host cells |
|---|---|---|---|
| I | <1 µg/mL | <1 µg/mL | 300 µg/mL |
| II | <1 | <1 | 300 |
| III | 3 | 3 | 150 |

-continued

Screening of Drugs in the Molt-3/HIV 1 Assay System

| Cmpd (Drug) | 50% reduction in syncytium formation | 50% reduction in p24 antigen | 50% kill of host cells |
|---|---|---|---|
| IV | 3 | 5 | 150 |
| V | 1 | <1 | 50 |
| VI | <1 | 2 | 50 |
| VII | 3 | 2 | 50 |
| VIII | <1 | 2 | 15 |
| IX | <1 | <1 | 10 |
| X | 2 | <1 | 5 |

Column 1 lists the identification number of each substance. The molecular structure of each substance appears in FIG. 1. Column 2 lists the approximate concentration of each compound that produces a 50% reduction of syncytial cells, relative to syncytial cell formation in an infected control that lacks the compound. The reported concentration is an average of the results obtained after 2, 3 and 4 days of incubation. Syncytial cell formation is an indicator of the cytopathic effect of HIV-1 infection in the host cell, and the results show that all of the compounds are effective at concentrations of 3 µg/mL or less.

Column 3 lists the approximate concentration of compound that produces a 50% reduction of soluble p24 antigen, as measured by a p24 capture immunoassay. The reported concentration is the result of measurements taken after 3 days of incubation, relative to infected controls lacking the compound. The p24 is a characteristic protein component of the HIV core, and its concentration is indicative of HIV concentration. The results show that all of the compounds are effective at concentrations of 5 µg/ml or less.

Column 4 lists the approximate concentration of compound that produces a 50% reduction in the viable population in uninfected host cells, compared to the population of surviving host cells in an uninfected control, measured after 5 days of incubation. The results show major differences in compound toxicity, ranging from low toxicity (I, II) to high toxicity (IX, X).

Discussion

The data show that all of these compounds are very active in reducing syncytial cell formation and p24 antigen levels. More significantly, a clear and obvious structure/activity correlation emerges with respect to toxicity of the compounds. The most highly toxic structures are IX and X which, under physiological conditions, are ionic and highly polar, ie., negatively charged carboxylate anion (X) and positively charged ammonium ion (IX).

Compounds I through VIII are non-ionic and constitute a series with generally decreasing polarity (increasing lipophilicity). The phenolic —OH group, common to all the structures, is weakly polar. Carboxylate ester groups (as in VI) are less polar, and the remaining structural components (alkyl, aryl, thioether) are least polar or non-polar. Compounds I through V comprise the clearest examples of progressive increments of alkyl and/or aryl groups (increasing lipophilicity) and the attendant decreases in toxicity.

Compound VIII is BHT, which has significant antiviral properties. Compound IV is probucol, whose antiviral properties are also illustrated herein. The present study establishes for the first time a correlation between structure and activity in this new class of antiviral agents, and a rational basis for the design of related compounds with improved "therapeutic window", ie., higher ratios of effectiveness to toxicity. Thus, on the basis of the assay system shown in the table above, analogs I and II have therapeutic windows that are at least ten times better than that of probucol (IV) and at least thirty times better than that of BHT (VIII).

Additional data are provided in FIGS. 3 and 4. While there is a large experimental variability in the results, all the analogs demonstrate substantial activity, albeit some consistently outperform the others.

An improved therapeutic window for an antiviral agent is of paramount importance for the successful treatment of viral infections, since efficacy can then be improved without increasing toxicity and other adverse side effects. It is further believed that these greatly improved antiviral analogs of BHT also exhibit improved utility in some of the therapeutic applications discussed herein, e.g., in the treatment of AIDS, CMV, Herpes, and SFV infections.

EXAMPLE III

Clinical Tests

Probucol was administered to 6 adult male documented HIV-positive (HIV+) patients, ranging in age from 31–44 years at the time of diagnosis, in dosages consistent with those prescribed for treatment of hypercholesterolemia. All patients receiving probucol took 1 gram per day (with the exception of Patient F, who received 4.5 g/day) in divided doses for individually-varying lengths of time, as indicated below. Each patient was examined regularly and clinical observations were made and recorded by the same treating physician each time, except where indicated otherwise. Samples of each patient's blood were collected periodically and were tested for levels of T helper cells ($CD4^+$ or T4) and T suppressor cells ($CD8^+$ or T8). The $CD4^+$:$CD8^+$ ratio ("R") was also calculated each time. Blood samples taken prior to the initiation of probucol treatment were analyzed and compared with the samples taken during the treatment phase. The same parameters were tested in all samples. The results of this testing are set out below:

| Patient | Date | Clin. Observations | Test Results |
|---|---|---|---|
| A | 5/6/88 | HIV+ (determined 2/26/88); asymptomatic. | T4 - 532<br>T8 - 1427<br>R - 0.37 |
|  | 5/7/88 | 1 g/day probucol begun, in divided doses. |  |
|  | 11/16/88 | Asymptomatic. | T4 - 1111<br>T8 - 1910<br>R - 0.58 |
|  | 5/5/89 | Asymptomatic. | T4 - 1161<br>T8 - 1879<br>R - 0.62 |
| B | 12/30/37 | AIDS with Kaposi's sarcoma. Received treatment with AZT prior to this time. AZT treatment was discontinued when patient became ill and developed a significant anemia. | T4 - 146<br>T8 - 393<br>R - 0.37 |
|  | 12/31/87 | 1 g/day probucol begun, in divided doses. |  |
|  | 4/8/88 | Kaposi's lesions smaller. | T4 - 263<br>T8 - 867<br>R - 0.30 |
|  | 12/1/88 | Lesions smaller and fewer in number. | T4 - 344<br>T8 - 847<br>R - 0.41 |
|  | 3/10/89 | Smaller lesions, and fewer in number. | T4 - 347<br>T8 - 583<br>R - 0.60 |
| C | 12/9/87 | ARC (AIDS-related complex): thrush, eczema and lymphadenopathy | T4 - 601<br>T8 - 978<br>R - 0.61 |
|  | 6/6/88 | Same as above | T4 - 533<br>T8 - 866<br>R - 0.62 |
|  | 6/7/88 | 1 g/day probucol begun, in divided doses. |  |
|  | 8/12/88 | Clinical symptoms improved. | T4 - 654<br>T8 - 515<br>R - 1.27 |
| D | 4/14/87 | Fatigue and rash* | T4 - 530<br>T8 - 2000<br>R - 0.30 |
|  | 6/30/87 | HIV+ (first documented)* |  |
|  | 7/1/87 | Increasing fatigue, rash and lymph node swelling* | T4 - 380<br>T8 - 1260<br>R - 0.30 |
|  | 10/28/87 | ARC: symptoms of thrush, eczema, and generalized lymphadenopathy.* | T4 - 247<br>T8 - 845<br>R - 0.30 |
|  | 11/5/87 | 1 g/day probucol begun, in divided doses. |  |
|  | 12/1/87 | Symptoms improved. | T4 - 457<br>T8 - 1828<br>R - 0.25 |
|  | 2/2/88 | Symptoms resolved. | T4 - 520<br>T8 - 1751<br>R - 0.30 |
|  | 6/7/88 | Symptom-free. | T4 - 512<br>T8 - 1536<br>R - 0.33 |
| E | 3/19/87 | HIV+; Asymptomatic.* | T4 - 710*<br>T8 - 1450*<br>R - 0.50* |
|  | 7/14/87 | Asymptomatic.* | T4 - 560*<br>T8 - 1230*<br>R - 0.50* |
|  | 2/3/88 | Asymptomatic.* | T4- 520*<br>T8 - 1102*<br>R - 0.47* |
|  | 4/27/88 | 1 g/day probucol begun, in divided doses. |  |
|  | 8/17/88 | Asymptomatic. | T4 - 679<br>T8 - 1462<br>R - 0.46 |
| F | 8/88 | Diagnosed with AIDS, Kaposi's sarcoma.* | T4 - 116<br>T8 - 1468<br>R - 0.08 |
|  | 9/88 | Treatment with AZT begun.* |  |
|  | 7/89 | Showing increased fatigue, HIV viremia, Kaposi's sarcoma fever (to 104–106) Weight loss: 20 lbs in one month. |  |
|  | 8/10/89 |  | T4 - 111 |
|  | 8/16/89 | AZT treatment stopped due to increasing HIV viremia. |  |
|  | 8/24/89 | Viral culture shows high concentration of HIV in the serum.** | T4 - 37 |

-continued

| Patient | Date | Clin. Observations | Test Results |
|---------|------|--------------------|--------------|
|  | 9/01/89 | Daily treatment begun with 1282-4-1, at 3 g/day. |  |
|  | 9/06/89 | Dosage increased to 4.5 g/day. |  |
|  | 9/14/89 |  | T4 - 45 |
|  | 9/21/89 | Afebrile; Kaposi's lesions shrinking. Weight gain of 15 lbs. over last 2 weeks. Viral culture of serum shows no detectable HIV.** |  |
|  | 11/7/89 |  | T4 - 85 |

*Information reported by prior treating physician.
**Culture method: obtain sample of peripheral blood, co-culture with phytohemagglutinin (PHA), measure increase of p24 vs. time. (See Lane, et al., "Acquired Immunodeficiency Syndrome and Related Diseases", in Rose, et al., eds., Manual of Clinical Laboratory Immunology, 3d Ed., Am. Soc. Microbiol., pp. 582–586, 1986.)

EXAMPLE IV

In Vitro Inhibition Tests

The following compounds were tested for their ability to inhibit HIV-1 virus infection in vitro. The compounds tested were: 1) probucol (2.5%); 2) 2,6 dicyclopentyl phenol (5%); 2,6 dicyclohexyl p-cresol (5%); 3) 4,4'-thiobis(6-tert-butyl-o-cresol) ("Ethanox® 322", 5%); 4) 4,4'-methylenebis(2,6-di-tert-butylphenol) ("Ethanox® 702", 1.25%); 5) 2,6-di-tert-butyl-α-dimethylamino-p-cresol ("Ethanox® 703", 5%); 6) 1,3,5-trimethyl-2,4,6-tris(3,5 -di-tert-butyl-4-hydroxybenzyl) benzene ("Ethanox® 330", 1.25%); and 7) 4,4'-methylenebis(2,6-di-tert-butylphenol) ("Ethanox® 728", 5%).

The compounds were diluted at 300, 200, 100, 30, 10, 3, and 1 microgram per milliliter (1 μg/ml) in Complete RPMI 1640 media (Gibco Laboratories, Grand Island, N.Y.). The compound dilutions were pre-incubated with an HIV-1 (10^3.6 titer) diluted at 1:100 and 1:1000 for one hour and then plated onto a CEM-SS infectivity assay. (See Nara, et al., *Aids Res. and Human Retroviruses* 3: 283–302 (1987), Mary Ann Liebert, publ., or Nara and Fischinger, *Nature* 332: 469–470 (1988)). The dilutions were also pre-incubated onto the cells for one hour, then inoculated with 1:100 and 1:1000 dilutions of the HIV-1(10^3.6 titer) that contained no compound. Inoculum was aspirated off the wells after one hour and the cells were maintained for five days with compound and media, then read for plaques.

Of the above-listed compounds, probucol displayed the most significant effects upon HIV-1 plaque formation. It was specifically observed that probucol significantly inhibited plaque formation at concentrations of about 200 μg/ml under both test conditions—i.e., when pre-incubated with the HIV and when pre-incubated with the cells, without significant toxicity to the cells. Probucol also appeared to inhibit plaque formation at concentrations of about 100 μg/ml, albeit the inhibition was not as marked as at twice the concentration. Again, there was no significant toxicity to the cells. The effects of the Ethanox® compounds tested were, in most cases, not always as marked as were those of probucol. Nevertheless, these phenolic antioxidants, and in particular, Ethanox® 728, demonstrated efficacy as antiviral and anti-retroviral agents.

EXAMPLE V

Effect of Drugs Against CMV in HS68 Cells

Virus Dilution (Log Factor) at Which a Cytopathic Effect is Seen.

| | Concentration of Drug, μg/ml | | | | | |
|---|---|---|---|---|---|---|
| Drug | 300 | 100 | 30 | 10 | 3 | 1 |
| TEST SET A | | | | | | |
| 1293-27-2 | T* | T | T | 4 | 5 | 6 |
| 1293-27-3 | T | T | T | >7 | >7 | 7 |
| 1293-24-4 | T | 7 | 7 | 7 | 6 | 7 |
| 1293-27-5 | T | 4 | 6 | 7 | 7 | 6 |
| Acyclovir | — | <2 | — | 7.0 | — | 7.0 |
| TEST SET B | | | | | | |
| 1297-12-3 | >6.5 | >6.5 | 6.5 | >6.5 | 6.5 | 6 |
| 1297-12-7 | >6.5 | >6.5 | >6.5 | >6.5 | >6.5 | >6.5 |
| 1297-12-8 | T | T | T | 6.5 | >6.5 | >6.5 |
| 1297-12-11 | T | T | T | T | 6 | 6.5 |
| 1297-12-12 | T | T | T | <4 | 6.5 | >6.5 |
| Acyclovir | — | <4 | — | 4.5 | — | 6.5 |

(*T denotes a toxic effect.)
[Test Set A is part of Test Set 3 (see FIGS. 3 and 4). Cytopathic effects were scored on day 9.]
[Test Set B is part of Test Set 4 (see FIGS. 3 and 4). Cytopathic effects were scored on day twelve.]

HS68 cells were preincubated with CMV for one hour at 37° C. at the indicated virsus dilution, and then exposed to drugs at concentrations ranging from 300 μg/ml to 1 μg/ml. The drugs were dispensed from 3% stock solutions in DMSO, and the final concentration of DMSO in each test well was ajusted to 1%. The wells were scored for cytopathic effects on the indicated days.

EXAMPLE VI

Effect of Drugs Against HSV-1 in HS68 Cells
Virus Dilution (Log Factor) at Which a Cytopathic Effect is Seen.

| | Concentration of Drug, g/ml | | | | | |
|---|---|---|---|---|---|---|
| Drug | 300 | 100 | 30 | 10 | 3 | 1 |
| TEST SET A | | | | | | |
| 1293-27-2 | 6 | 7 | 7 | 8 | 7 | 7 |
| 1293-27-3 | T | T | T | 7 | 7 | 7 |
| 1293-27-4 | 8 | 8 | 7 | 7 | 7 | 7 |
| 1293-27-5 | T | 7 | 7 | 7 | 7 | 7 |
| Acyclovir | — | <4 | — | <4 | — | 5 |
| TEST SET B | | | | | | |
| 1297-12-3 | 7.5 | 7.5 | 7.5 | 7.5 | 7.5 | 7.5 |
| 1297-12-7 | 7.5 | 7 | 7 | 7.5 | 7.5 | 7 |
| 1297-12-8 | T | T | 7.5 | 7.5 | 7.5 | 7.5 |
| 1297-12-11 | T | T | T | T | 7.5 | >7.5 |
| 1297-12-12 | T | T | 7 | 7.5 | 7.5 | 7 |
| Acyclovir | — | 5 | — | 5 | — | 5 |

[Test Set A is part of Test Set 3 (see FIGS. 3 and 4). Cytopathic effects were scored on day three.]
[Test Set B is part of Test Set 4 (see FIGS. 3 and 4). Cytopathic effects were scored on day three.]

HS68 cells were preincubated with HSV-1 for one hour at 37° C. at the indicated virus dilution, and then exposed to drugs at concentrations ranging from 300 g/ml to 1 g/ml. The drugs were dispensed from 3% stock solutions in DMSO, and the final concentration of DMSO in each test well was adjusted to 1%. The wells were scored for cytopathic effects on the indicated days.

Although the invention has been described in the context of particular embodiments, it is intended that the scope of coverage of the patent not be limited to those particular embodiments, but be determined by reference to the following claims.

What is claimed is:

1. A method for inhibiting infectivity of a virus comprising contacting the virus with an effective amount of a compound having the formula:

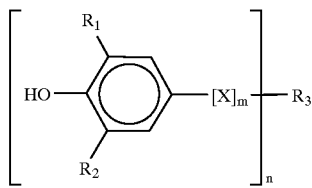

wherein m=1; n=2; X is sulfur; $R_1$ is hydrogen or a lower alkyl from 1–6 carbon atoms; $R_2$ is a lower alkyl from 1–6 carbon atoms; and $R_3$ is an alkyl, an aryl or a mixed alkyl/aryl, containing from 1–25 carbon atoms.

2. The method of claim 1 wherein the virus is HIV.

3. The method of claim 1 wherein the virus is cytomegalovirus.

4. The method of claim 1 wherein the virus is Herpes Simplex virus.

5. The method of claim 1 wherein said administering is ex vivo.

6. A method of inhibiting infectivity of a virus in a composition comprising blood, a blood component, cell culture or a component of cell culture comprising administering an effective antiviral amount of a compound having the formula:

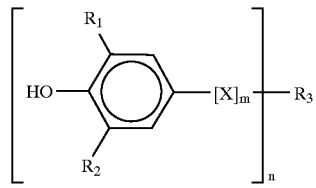

wherein m=1; n=2; X is sulfur; $R_1$ is hydrogen or a lower alkyl from 1–6 carbon atoms; $R_2$ is a lower alkyl from 1–6 carbon atoms; and $R_3$ is an alkyl, an aryl or a mixed alkyl/aryl, containing from 1–25 carbon atoms.

7. The method of claim 6 wherein the virus is HIV.

8. The method of claim 6 wherein the virus is cytomegalovirus.

9. The method of claim 6 wherein the virus is Herpes Simplex virus.

* * * * *